(12) United States Patent
Takahashi et al.

(10) Patent No.: US 10,006,068 B2
(45) Date of Patent: Jun. 26, 2018

(54) METHOD FOR PRODUCING PULVERULENT CERAMIDE

(71) Applicants: Nippon Beet Sugar Manufacturing., Co., LTD., Minato-ku (JP); T. HASEGAWA CO., LTD., Chuo-ku (JP)

(72) Inventors: Keisuke Takahashi, Obihiro (JP); Taizo Nagura, Minato-ku (JP); Hiroto Kikuchi, Obihiro (JP); Teruhisa Ohashi, Kawasaki (JP); Natsumi Suzuki, Kawasaki (JP); Tadashi Yoshimoto, Kawasaki (JP); Tomohiro Hosogai, Kawasaki (JP)

(73) Assignees: Nippon Beet Sugar Manufacturing., Co., Ltd., Minato-ku (JP); T. HASEGAWA CO., LTD., Chuo-ku (JP)

( * ) Notice: Subject to any disclaimer, the term of this patent is extended or adjusted under 35 U.S.C. 154(b) by 0 days. days.

(21) Appl. No.: 14/908,764

(22) PCT Filed: Jul. 29, 2014

(86) PCT No.: PCT/JP2014/069981
§ 371 (c)(1),
(2) Date: Jan. 29, 2016

(87) PCT Pub. No.: WO2015/016234
PCT Pub. Date: Feb. 5, 2015

(65) Prior Publication Data
US 2016/0160248 A1 Jun. 9, 2016

(30) Foreign Application Priority Data

Jul. 30, 2013 (JP) .................. 2013-158127

(51) Int. Cl.
| | |
|---|---|
| C12P 13/02 | (2006.01) |
| C12P 7/64 | (2006.01) |
| C12P 19/44 | (2006.01) |
| A23D 9/013 | (2006.01) |
| A23D 9/05 | (2006.01) |

(52) U.S. Cl.
CPC ............. *C12P 13/02* (2013.01); *A23D 9/013* (2013.01); *A23D 9/05* (2013.01); *C12P 19/44* (2013.01)

(58) Field of Classification Search
None
See application file for complete search history.

(56) References Cited

U.S. PATENT DOCUMENTS

| | | | |
|---|---|---|---|
| 2010/0273727 A1 | 10/2010 | Mukai et al. | |
| 2010/0330648 A1* | 12/2010 | Harvey | C12M 21/12 435/209 |

FOREIGN PATENT DOCUMENTS

| | | | |
|---|---|---|---|
| JP | 2005-120321 A | | 5/2005 |
| JP | 2005120321 A | * | 5/2005 |
| JP | 2008-274106 A | | 11/2008 |
| JP | 2008274106 A | * | 11/2008 |
| WO | 2009/084275 A1 | | 7/2009 |

OTHER PUBLICATIONS

"Dextrin"; Remington: The Science of Pharmacy, 21st Ed.; Lippincott Williams & Wilkins: PA, 2005; p. 1085.*
Joshi et al., "Purification and characterization of pectinase produced from Apple pomace and evaluation of its efficacy for fruit juice extraction and clarification", Indian Journal of Natural Products and Resources 2011, vol. 2, pp. 189-197.*
Hendrickson et al., "Emulsions", Remington: The Science of Pharmacy, 21st Ed.; Lippincott Williams & Wilkins: PA, 2005; pp. 759-767.*
Mio, et al., "Double-Blind Study on Effects of Glucosyl Ceramide in Beet Extract on Skin Elasticity and Fibronectin Production in Human Dermal Fibroblasts", Anti-Aging Medicine, Jul. 13, 2010, vol. 7, No. 11, pp. 129-142 (14 pages).
International Search Report dated Nov. 4, 2014 for PCT/JP2014/069981 filed on Jul. 29, 2014.

* cited by examiner

*Primary Examiner* — Michelle F. Paguio Frising
(74) *Attorney, Agent, or Firm* — Oblon, McClelland, Maier & Neustadt, L.L.P.

(57) ABSTRACT

Disclosed herein is a pulverulent ceramide producing method that enables easily and efficiently extracting and separating ceramide from sugar beet pulp, and efficiently pulverizing the ceramide by spray drying. The pulverulent ceramide can be efficiently obtained by a process that includes concentrating, with and/or without adding water, a sugar beet pulp ethanol extract obtained by extraction of a sugar beet pulp (for example, such as a beet fiber) with ethanol, adding pectinase to the resulting concentrate and performing an enzymatic reaction, performing emulsification after inactivating the enzyme, and pulverizing the resulting emulsion using spray drying.

20 Claims, 3 Drawing Sheets

[FIG. 1]
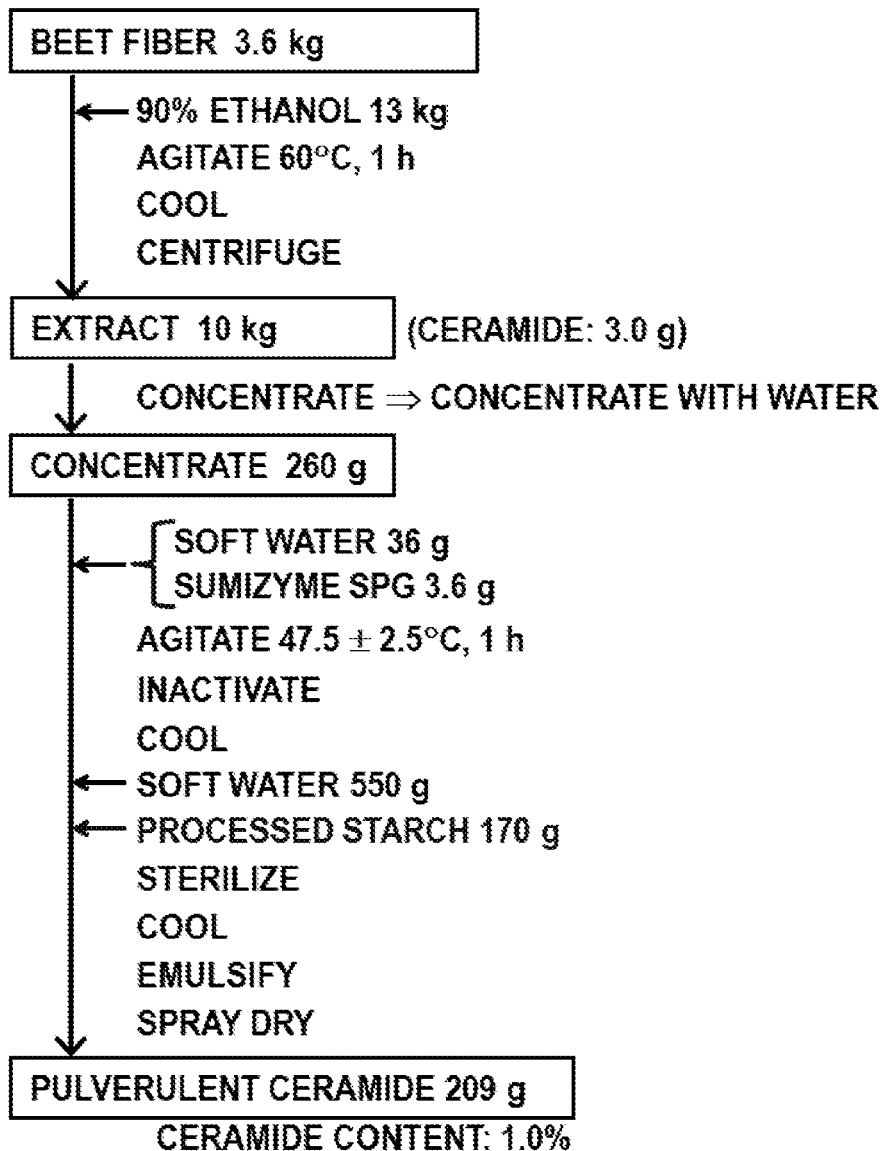

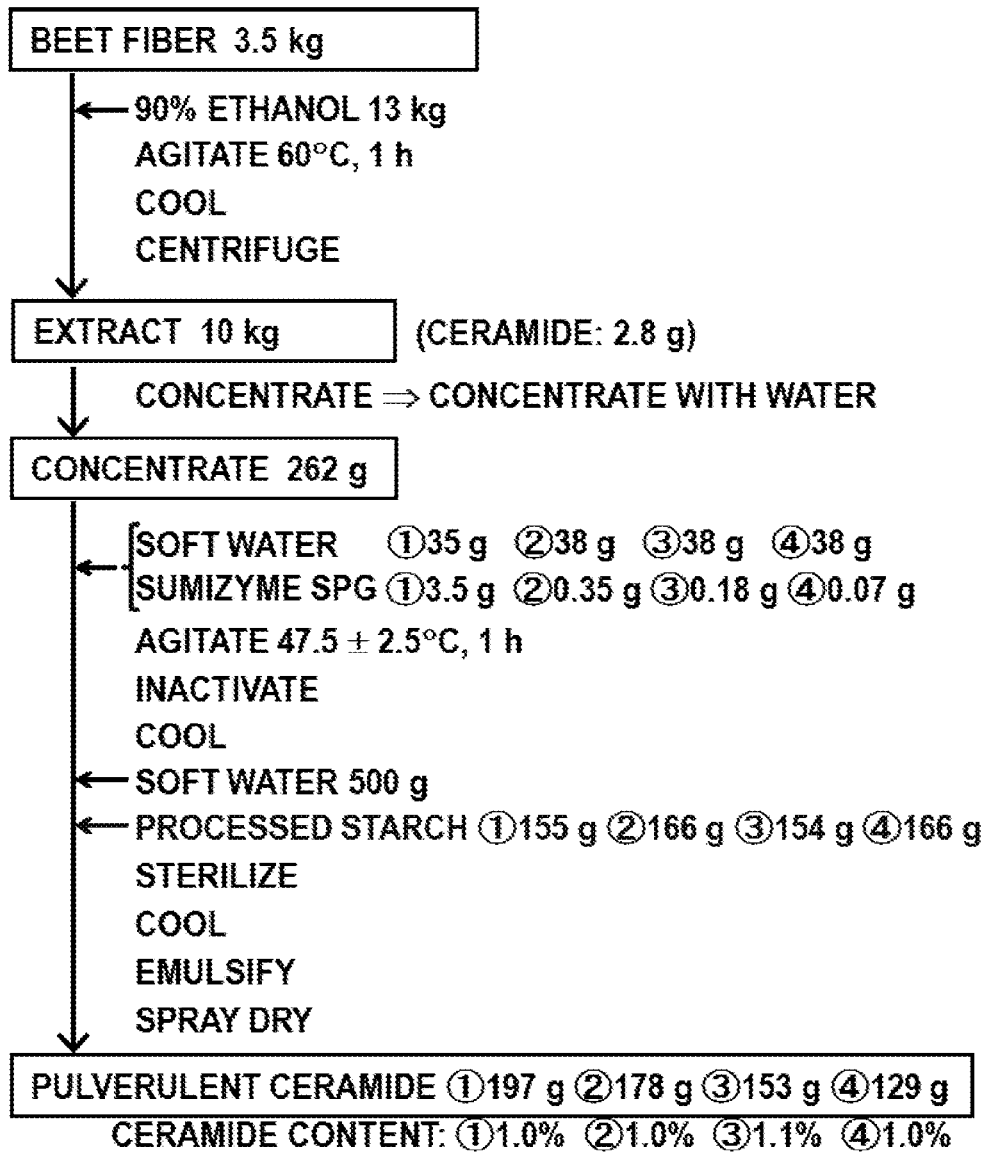
[FIG. 2]

[FIG. 3]
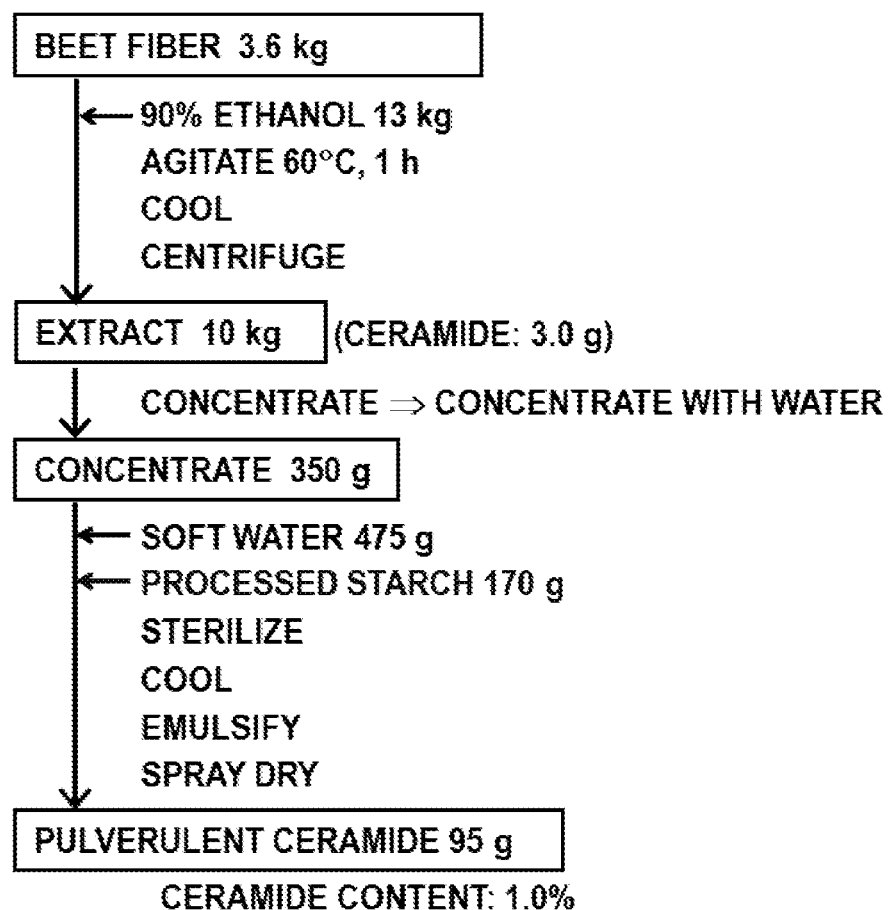

METHOD FOR PRODUCING PULVERULENT CERAMIDE

TECHNICAL FIELD

The present invention relates to methods for producing pulverulent ceramide from sugar beet pulp. Specifically, the present invention relates to methods for producing pulverulent ceramide from a sugar beet pulp ethanol extract through ceramide separation, purification, and spray drying.

BACKGROUND ART

Sugar beet (beet) is a plant useful as a raw material for the extraction of not only sucrose but various functional components (such as raffinose, and betaine). Lately, sugar beet and sugar beet pulp (for example, a fibrous residue after the extraction of sucrose from a sugar beet root) also have been used as raw material for ceramide (glucosylceramide) extraction.

Plant-derived glucosylceramides are a type of sphingoglycolipid which consists of a ceramide with one glucose molecule, and are known to exhibit skin function improving effects (e.g., moisture retention, and anti-atopic effect). This component has attracted interest not only as a raw material of cosmetics but a raw material of food (for oral ingestion).

Some methods have been disclosed that produce a glucosylceramide-containing product from plant raw materials such as cereals and sugar beet (Patent Documents 1 to 4). However, these are all concerned with extraction efficiency from raw material, and merely describe an example of vacuum drying for pulverization. None of these publications describes pulverization by spray drying, or how to make spray drying more efficient.

On the other hand, ceramide extraction from plants involves large amounts of components other than sphingoglycolipids, and the purification and pulverization are not possible effectively. For industrial mass production, spray drying represents the most desirable in pulverization methods. However, it is often difficult for a ceramide-containing liquid to efficiently spray dry because of the nature of the liquid.

Under these circumstances, there is a need in the art to develop a pulverulent ceramide producing method that can produce a pulverulent ceramide through efficient spray-drying pulverization of a ceramide-containing liquid extracted from a plant raw material.

PRIOR ART DOCUMENTS

Patent Document

Patent Document 1: JP-A-11-092781
Patent Document 2: JP-A-11-193238
Patent Document 3: JP-A-2000-080394
Patent Document 4: WO2011/016558

SUMMARY OF THE INVENTION

Problem to be Solved by the Invention

It is an object of the present invention to provide a pulverulent ceramide producing method that enables easily and efficiently extracting and separating ceramide from sugar beet pulp, and efficiently pulverizing the ceramide by spray drying.

Means for Solving

The present inventors conducted intensive studies to achieve the foregoing object, and found that a pulverulent ceramide can be efficiently obtained through a process that includes concentrating, with and/or without adding water, a sugar beet pulp ethanol extract obtained through extraction of sugar beet pulp with ethanol; adding pectinase to thus obtained concentrate and performing an enzymatic reaction; performing emulsification after inactivating the enzyme; and pulverizing the resulting emulsion using spray drying. The present invention was completed on the basis of this finding.

Specifically, the following represents an exemplary embodiment of the present invention.

(1) A method for producing pulverulent ceramide, the method comprising:
concentrating, with and/or without adding water, a sugar beet pulp ethanol extract obtained through extraction of a sugar beet pulp with ethanol;
adding pectinase to thus obtained concentrate and performing an enzymatic reaction;
performing emulsification after inactivating the enzyme; and
pulverizing the resulting emulsion using spray drying.

(2) The method according to (1), wherein the enzymatic reaction is performed at a temperature of 10 to 70° C. for 6 minutes or more.

(3) The method according to (2), wherein the enzymatic reaction is performed at a temperature of 45 to 50° C. for 0.5 to 2 hours.

(4) The method according to any one of (1) to (3), wherein the pectinase is added in 0.0002 weight % or more of an amount of the raw material sugar beet pulp.

(5) The method according to (4), wherein the pectinase is added in 0.005 to 0.2 weight % of an amount of the raw material sugar beet pulp.

(6) The method according to any one of (1) to (5), wherein an excipient is added as a pulverization auxiliary agent before the emulsification.

(7) The method according to (6), wherein a processed starch is added as the excipient.

(8) A method for improving a spray drying yield of a ceramide-containing emulsion, the method comprising:
concentrating, with and/or without adding water, a sugar beet pulp ethanol extract obtained by extracting sugar beet pulp using ethanol;
adding pectinase to the resulting concentrate and performing an enzymatic reaction to lower the viscosity of the concentrate; and
emulsifying the low-viscosity concentrate to obtain an emulsion.

Advantageous Effects of Invention

The present invention enables easily and efficiently producing pulverulent ceramide from sugar beet pulp in high yield, without unnecessarily lowering the spray drying yield. The method of the present invention has considerable improvements over the methods of related art in convenience and spray drying yield, and is suited for industrial mass production of pulverulent ceramide.

BRIEF DESCRIPTION OF DRAWINGS

FIG. 1 is a diagram representing the procedure of the pulverulent ceramide production from beet fiber (BF) performed in Example 1.

FIG. 2 is a diagram representing the procedure of the pulverulent ceramide production from beet fiber (BF) performed in Example 2. The enzyme (Sumizyme SPG) was used in the same amount as in Example 1 (control), and in 1/10, 1/20, and 1/50 of Example 1, from the left.

FIG. 3 is a diagram representing the procedure of the pulverulent ceramide production from beet fiber (BF) performed in Reference Example.

DESCRIPTION OF EMBODIMENTS

The present invention is concerned with a method for extracting, purifying, and pulverizing ceramide from raw material sugar beet pulp. As used herein, "sugar beet pulp" refers to fiber-containing materials obtained from root portions of beet (sugar beet), and encompasses the residues (fibrous residues) obtained after the collection of sugar components such as sucrose from sugar beet roots known as sugar raw material, or the materials (for example, beet fiber) obtained after drying and/or comminuting such residual materials. The sugar beet pulp used in the present invention is used preferably after the sugar component is sufficiently extracted (or removed), for example, after removing the sugar component with a beet sugar manufacturing apparatus used in places such as sugar factories.

As an example of a method for preparing a beet fiber, a sugar beet root is cut into a form of narrow strips, or milled or squeezed. The root is then dipped in warm water, and the residue after sufficiently extracting and removing soluble components such as sucrose is subjected to necessary processes such as decoloring, deodorizing, drying, comminution, and sieving. A large proportion of the fiber structure in the beet fiber becomes destroyed after sufficient drying and/or disruption, and such beet fibers are more preferred for use as a raw material for the extraction of the active component with ethanol.

In the present invention, ethanol extraction is performed with the sugar beet pulp obtained as above. Instead of ethanol, other alcohols may be used as extraction solvent, provided that properties such as polarity are the same. However, the method excludes use of non-alcohol solvents (such as hot water, and acids) because non-alcohol solvents are unsuited for ceramide extraction.

As an example of ethanol extraction, ethanol (90% or higher concentrations) is mixed in 0.1 to 10 times or more (for example, 1 to 10 times, and 2 to 5 times) the weight of the sugar beet pulp, and the solid component is removed (for example, by centrifugation, or filtration with a filter) after being extracted at a temperature of 0 to 78° C., preferably 10 to 70° C., further preferably 40 to 60° C. When ethanol is used as the solvent in amount of less than 5 times, reflux extraction may be performed with, for example, a Soxhlet extractor to extract the active component in sufficient amounts. It is preferable to also perform reflux extraction when ethanol is used in 5 times or more.

The sugar beet pulp ethanol extract obtained as above is directly concentrated, and/or concentrated after adding soft water. The extract may be concentrated using an ordinary method, or more preferably concentrated under reduced pressure or vacuum. This step removes most of ethanol used as the extraction solvent, but does not remove most of the water so that a concentrated aqueous solution is produced.

Thereafter, pectinase is added to the concentrate, and an enzymatic reaction is performed. Any pectinase may be used for the enzymatic reaction step, as long as it has the catalytic ability to decompose pectin. It is, for example, preferable to use pectinases derived from *Aspergillus niger* origin. A commercially product can be used as such enzymes. Examples include Sclase N, and Sclase S (Mitsubishi-Kagaku Foods Corporation), Sumizyme SPC, and Sumizyme SPG (Shin-Nihon Kagaku Kogyo Corporation), and Ultrazym, and Vinozym (Novozymes Japan).

The enzymatic reaction is performed with the pectinase added in 0.0002 weight % or more, preferably 0.005 to 0.2 weight % with respect to the amount of the raw material sugar beet pulp, under neutral conditions with an enzymatic reaction temperature of 10 to 70° C. (preferably 45 to 50° C.) for 6 minutes or more (preferably 0.5 to 2 hours). However, the reaction conditions are not entirely limited to these ranges, and may be appropriately adjusted according to such factors as the type of the raw material used, and the state of the concentrate. The enzyme treatment can lower the viscosity of the concentrate.

The enzymatic reaction is followed by enzyme inactivation (for example, performed at 85 to 95° C. for 1 to 5 min), cooling, and emulsification. The emulsification may be performed with, for example, a high-speed rotary mixer (for example, at 5000 to 10000 rpm for 10 to 30 min), or a high-pressure emulsifier (for example, at 0.01 to 10 MPa). Preferably, an excipient is added as a pulverization auxiliary agent before the emulsification. Sterilization may be performed before and/or after the emulsification, as required.

The excipient is preferably a processed starch, and may be, for example, dextrin, powdered oil, or cellulose. However, the excipient is not entirely limited to these, and may be appropriately selected and adjusted according to such factors as the enzymatic reaction liquid, and the emulsion state.

The resulting emulsion is pulverized by spray drying. The spray drying is not particularly limited, and may be performed with a variety of known devices (for example, devices that use nozzle spraying or centrifugal spraying, and collect particles by using the take-up method, the blow-down method, or one-time capturing with a bag filter). In this way, a fine powder can be obtained in a short time period. In the present invention, the ceramide-containing emulsion used for spray drying has properties that are highly suited for spray drying, and involves only a small loss in spray drying (for example, a spray drying yield of 75% or more, or even 85% or more can be achieved).

As described above, the present invention enables easy and efficient industrial production of pulverulent ceramide from sugar beet pulp. On the other hand, in the process of the present invention, the emulsion viscosity is very low, and the emulsion properties remain stable before spray drying. Therefore, this is very effective in terms of improving not only the ceramide collection rate at the time of spray drying but the spray drying yield itself.

Examples of the present invention are described below. The present invention is not limited to the following Examples, and may be implemented in various modifications within the technical idea of the present invention.

EXAMPLE 1

(Production of Pulverulent Ceramide from Beet Fiber I)

The following experiment was conducted for the production of pulverulent ceramide through extraction from beet fiber as a raw material.

First, 90% ethanol (13 kg) was added to dry beet fiber (3.6 kg), and the fiber was extracted for 1 hour while being agitated at 60° C. The beet fiber ethanol extract (10 kg) after solid-liquid separation (centrifugation) was concentrated under reduced pressure, and concentrated under reduced pressure again after adding water. Soft water (36 g) was added at the time of the liquid amount reaching 260 g. To the concentrate was then added pectinase (Sumizyme SPG; Shin-Nihon Kagaku Kogyo Corporation) in 0.1% (3.6 g) of the amount of the raw material beet fiber, and an enzyme treatment was performed to lower the viscosity of the concentrate. The enzyme treatment was performed for 1 hour while agitating the mixture at 47.5±2.5° C. The concentrate was cooled after enzyme inactivation (90° C., 2 min), and soft water (550 g) and processed starch (170 g) were added, and dissolved (suspended) by being agitated. After sterilizing (90° C., 2 min) and cooling the solution, emulsification was performed (Primix product TK Homomix; 6000 rpm, 15 min), and an emulsion (946 g) was obtained through filtration (100 mesh). The emulsion was pulverized with a spray drier Type L-8 (Ohkawara Kakohki Corporation).

Thus obtained pulverulent ceramide weighed 209 g, and had a ceramide content of 1.0%. The yield was about 70% of the ceramide (3.0 g) contained in the beet fiber extract. The spray drying yield was about 80%. FIG. 1 shows the procedures, yields, and other conditions of the production tested in this Example.

EXAMPLE 2

(Production of Pulverulent Ceramide from Beet Fiber II)

The following experiment was conducted to examine the amount of pectinase added in the pulverulent ceramide production from beet fiber.

First, 90% ethanol (13 kg) was added to dry beet fiber (3.5 kg), and the fiber was extracted for 1 hour while being agitated at 60° C. The beet fiber ethanol extract (10 kg) after solid-liquid separation (centrifugation) was concentrated under reduced pressure, and concentrated under reduced pressure again after adding water. Soft water was added in the amounts shown in FIG. 2 (4 patterns) at the time of the liquid amount reaching 262 g. To the concentrate was then added pectinase (Sumizyme SPG; Shin-Nihon Kagaku Kogyo Corporation) in the amounts shown in FIG. 2, and the enzyme treatment was performed to lower the viscosity of the concentrate. The enzyme treatment was performed for 1 hour while agitating the mixture at 47.5±2.5° C. The concentrate was cooled after enzyme inactivation (92° C., 2 min), and soft water (500 g) and processed starch (the amounts shown in FIG. 2) were added, and dissolved (suspended) by being agitated. After sterilizing (92° C., 2 min) and cooling the solution, emulsification was performed (Primix product TK Homomix; 6000 rpm, 15 min), and an emulsion was obtained through filtration (100 mesh). The emulsion was pulverized with a spray drier Type L-8 (Ohkawara Kakohki Corporation).

Thus obtained pulverulent ceramide weighed 197 g in the control (the same conditions as in Example 1), 178 g with enzyme $1/10$, 153 g with enzyme $1/20$, and 129 g with enzyme $1/50$, and had a ceramide content of 1.0% in the control, 1.0% with enzyme $1/10$, 1.1% with enzyme $1/20$, and 1.0% with enzyme $1/50$. The yield was about 70% in the control, about 64% with enzyme $1/10$, about 60% with enzyme $1/20$, and about 46% with enzyme $1/50$ with respect to the ceramide (2.8 g) contained in the beet fiber extract. The spray drying yield was about 83% in the control, about 78% with enzyme $1/10$, about 65% with enzyme $1/20$, and about 52% with enzyme $1/50$. There results showed that desirable yields and desirable powder yields can be obtained with enzyme amounts as small as $1/10$ of the amount used in Example. FIG. 2 shows the procedures, yields, and other conditions of the production tested in this Example.

REFERENCE EXAMPLE

For comparison, the following experiment was conducted for the production of pulverulent ceramide through extraction from a raw material beet fiber, without enzyme treatment.

First, 90% ethanol (13 kg) was added to dry beet fiber (3.6 kg), and the fiber was extracted for 1 hour while being agitated at 60° C. The beet fiber ethanol extract (10 kg) after solid-liquid separation (centrifugation) was concentrated under reduced pressure, and concentrated under reduced pressure again after adding water. Soft water (475 g) and processed starch (170 g) were added at the time of the liquid amount reaching 350 g, and dissolved (suspended) by being agitated. After sterilizing (90° C., 2 min) and cooling the solution, emulsification was performed (Primix product TK Homomix; 6000 rpm, 15 min), and an emulsion was obtained through filtration (100 mesh). The emulsion was pulverized with a spray drier Type L-8 (Ohkawara Kakohki Corporation).

Thus obtained pulverulent ceramide weighed 95 g, and had a ceramide content of 1.0%. The yield was about 32% of the ceramide (3.0 g) contained in the beet fiber extract. The spray drying yield was about 36%. FIG. 3 shows the procedures, yields, and other conditions of the production tested in this Example.

These results demonstrated that the spray drying yield can improve to 78% or more, or even 80% or more, and the pulverulent ceramide can be obtained in high yield with the process that includes extracting a beet fiber with ethanol, adding water to thus obtained beet fiber ethanol extract, concentrating thus obtained mixture (removing solvent), adding pectinase to the concentrate and performing an enzymatic reaction, performing emulsification after inactivating the enzyme, adding a processed starch, and sterilizing the mixture, and pulverizing the resulting emulsion using spray drying.

The present invention can be summarized as follows.

The present invention is intended to provide a pulverulent ceramide producing method that enables easily and efficiently extracting and separating ceramide from sugar beet pulp, and efficiently pulverizing the ceramide by spray drying.

The pulverulent ceramide can be efficiently obtained through a process that includes concentrating, with and/or without adding water, a sugar beet pulp ethanol extract obtained through extraction of a sugar beet pulp (for example, such as a beet fiber) with ethanol, adding pectinase to the concentrate and performing an enzymatic reaction, performing emulsification after inactivating the enzyme, and pulverizing the resulting emulsion using spray drying.

The invention claimed is:

1. A method for producing a pulverulent ceramide, the method comprising:
concentrating, with or without adding water, a sugar beet pulp ethanol extract to obtain a concentrate, wherein the sugar beet pulp ethanol extract is obtained by a process comprising mixing ethanol and a raw sugar beet pulp material and performing solid-liquid separation to remove a solid component from a mixture of the ethanol and the raw sugar beet pulp material;

adding pectinase to the concentrate such that an enzymatic reaction is performed to degrade pectin and that the viscosity of the concentrate is lowered;

inactivating the pectinase;

emulsifying the product of the enzymatic reaction to produce an emulsion; and spray drying the emulsion to produce a pulverant ceramide.

2. The method according to claim 1, wherein the enzymatic reaction is performed at a temperature of 10 to 70° C. for 6 minutes or more.

3. The method according to claim 1, wherein the enzymatic reaction is performed at a temperature of 45 to 50° C. for 0.5 to 2 hours.

4. The method according to claim 3, wherein the pectinase is added in 0.005 to 0.2 weight % of an amount of the raw material sugar beet pulp.

5. The method according to claim 3, wherein the pectinase is added in 0.01 to 0.1 weight % of an amount of the raw material sugar beet pulp.

6. The method according to claim 1, wherein the pectinase is added in 0.0002 weight % or more of an amount of the sugar beet pulp material.

7. The method according to claim 1, wherein the pectinase is added in 0.005 to 0.2 weight % of an amount of the raw sugar beet pulp material.

8. The method according to claim 1, wherein an excipient is added as a pulverization auxiliary agent before the emulsifying.

9. The method according to claim 8, wherein the excipient comprises a processed starch.

10. The method according to claim 1, wherein the concentrate comprises water.

11. The method according to claim 1, further comprising: mixing ethanol and a raw material sugar beet pulp; and performing solid-liquid separation to remove a solid component from a mixture of the ethanol and the raw sugar beet pulp material to produce the sugar beet pulp ethanol extract.

12. The method according to claim 1, wherein the pectinase is added in 0.01 to 0.1 weight % of an amount of the raw sugar beet pulp material.

13. The method according to claim 1, wherein the inactivating of the pectinase comprises heating the product of the enzymatic reaction at a temperature of from 85 to 95° C. for 1 to 5 minutes.

14. The method according to claim 1, wherein the emulsifying is performed by treating the product of the enzymatic reaction with a high-speed rotary mixer or a high-pressure emulsifier.

15. The method according to claim 1, wherein the emulsifying is performed by mixing the product of the enzymatic reaction at 5000 to 10000 rpm for 10 to 30 minutes.

16. The method according to claim 1, wherein the emulsifying is performed by treating the product of the enzymatic reaction at a pressure of from 0.01 to 10 MPa.

17. The method according to claim 1, wherein the solid-liquid separation is performed by centrifugation.

18. The method according to claim 1, wherein the solid-liquid separation is performed by filtration.

19. A method for improving a spray drying yield of a ceramide-containing emulsion, the method comprising:

concentrating, with or without adding water, a sugar beet pulp ethanol extract to obtain a concentrate, wherein the sugar beet pulp ethanol extract is obtained by a process comprising mixing ethanol and a raw sugar beet pulp material and performing solid-liquid separation to remove a solid component from a mixture of the ethanol and the raw sugar beet pulp material;

adding pectinase to the concentrate such that an enzymatic reaction is performed to lower the viscosity of the concentrate; and emulsifying the low-viscosity concentrate to obtain an emulsion containing ceramide.

20. A method for producing a pulverulent ceramide, the method comprising:

concentrating, without adding water, a sugar beet pulp ethanol extract obtained through extraction of a sugar beet pulp with ethanol to obtain a concentrate;

adding pectinase to the concentrate such that an enzymatic reaction is performed to degrade pectin and that the viscosity of the concentrate is lowered;

inactivating the pectinase;

emulsifying the product of the enzymatic reaction to produce an emulsion; and spray drying the emulsion to produce a pulverant ceramide.

* * * * *